United States Patent
Al-Taie et al.

(10) Patent No.: US 8,852,535 B2
(45) Date of Patent: Oct. 7, 2014

(54) DEVICE AND METHOD FOR MEASURING ELEMENTAL SULFUR IN GAS IN GAS LINES

(75) Inventors: Ihsan Al-Taie, Dhahran Hills (SA); Abdulaziz A. Al-Mathami, Dammam (SA); Helal M. Al-Mutairi, Dammam (SA)

(73) Assignee: Saudi Arabian Oil Company (SA)

( * ) Notice: Subject to any disclaimer, the term of this patent is extended or adjusted under 35 U.S.C. 154(b) by 2375 days.

(21) Appl. No.: 10/957,564

(22) Filed: Oct. 1, 2004

(65) Prior Publication Data

US 2005/0095721 A1 May 5, 2005

Related U.S. Application Data

(60) Provisional application No. 60/508,507, filed on Oct. 3, 2003.

(51) Int. Cl.
*B01L 9/00* (2006.01)
*G01N 1/22* (2006.01)
*C01B 17/02* (2006.01)
*G01N 33/00* (2006.01)
*G01N 1/10* (2006.01)
*G01N 1/40* (2006.01)

(52) U.S. Cl.
CPC ...... *C01B 17/021* (2013.01); *G01N 2001/1062* (2013.01); *G01N 2001/4033* (2013.01); *G01N 1/2214* (2013.01); *G01N 1/2247* (2013.01); *G01N 2001/2282* (2013.01); *G01N 1/2202* (2013.01); *G01N 1/22* (2013.01); *G01N 33/0044* (2013.01)
USPC ............................ 422/565; 422/544; 422/560

(58) Field of Classification Search
USPC .......................... 422/100–104, 547, 560, 565; 73/863.11, 863.12, 863.21, 863.22, 73/863.23
See application file for complete search history.

(56) References Cited

U.S. PATENT DOCUMENTS 3,797,319 A * 3/1974 Abe .............................. 73/865.5

3,938,390 A 2/1976 Grey
(Continued)

FOREIGN PATENT DOCUMENTS

DE 197 11 349 A1 9/1998
EP 0 959 338 A2 11/1999
(Continued)

OTHER PUBLICATIONS

Rohrback Cosasco Systems, Model 50 COSACO® Two-Inch System Access Fitting Assemblies, www.rohrbackcosasco.com, 1 page.
(Continued)

*Primary Examiner* — Jill Warden
*Assistant Examiner* — Dwayne K Handy
(74) *Attorney, Agent, or Firm* — Bracewell & Giuliani LLP; Constance Gail Rhebergen; Brad Y. Chin

(57) ABSTRACT

A device and method for measuring the level of elemental sulfur present in a gas in a gas line. The device may include: an access fitting detachably connectable with the gas line, the access fitting having a first end and a second end; a probe detachably connectable to at least one end of the access fitting and adapted for insertion into a gas flow stream from the gas line to recover condensed components on the probe's outer surface; and a piping partially disposed within the probe for providing a cooling medium to the probe. The method may include the steps of: collecting a sample of elemental sulfur-containing gas from the gas line, wherein the sample is collected on an outer surface of a probe by condensing some or all of the elemental sulfur-containing gas in the gas line on a surface of the probe while the gas line is operational, the probe being removably placed into a gas flow stream from the gas line; separating the elemental sulfur from other species in the sample into an amount of elemental sulfur; and analyzing the amount of elemental sulfur collected. The device and method of the present invention for measuring the level of elemental sulfur present in a gas in a gas line, when compared with previously proposed devices and methods, has the advantages of: providing an accurate measurement of elemental sulfur, being able to distinguish between free elemental sulfur and sulfur in other sulfur-containing chemicals, and being practical and effective for use in process plant applications, particularly pressurized gas lines.

7 Claims, 3 Drawing Sheets

(56) References Cited

U.S. PATENT DOCUMENTS

| | | | |
|---|---|---|---|
| 4,191,541 A | | 3/1980 | Jenkins |
| 4,218,918 A | | 8/1980 | Ueno et al. |
| 4,342,234 A | * | 8/1982 | Bernath .................... 73/863.12 |
| 4,535,639 A | | 8/1985 | Bianchini et al. |
| 4,697,465 A | * | 10/1987 | Evans et al. .................. 73/866.5 |
| 4,764,024 A | | 8/1988 | Ryan |
| 5,170,661 A | * | 12/1992 | Lewis et al. .................. 73/61.62 |
| 5,308,979 A | | 5/1994 | Villa-Aleman |
| 5,331,846 A | * | 7/1994 | Hurley et al. ..................... 73/86 |
| 5,493,923 A | * | 2/1996 | Balfanz et al. ............. 73/863.21 |
| 5,520,048 A | | 5/1996 | Traina et al. |
| 5,777,241 A | * | 7/1998 | Evenson .................... 73/863.11 |
| 5,807,410 A | | 9/1998 | Boorsboom et al. |
| 6,141,972 A | * | 11/2000 | Evans ........................... 62/50.2 |
| 6,318,192 B1 | | 11/2001 | Carbone |
| 6,869,800 B2 | | 3/2005 | Torgerson et al. |
| 2002/0121147 A1 | | 9/2002 | Amory et al. |

FOREIGN PATENT DOCUMENTS

| | | |
|---|---|---|
| EP | 1 346 831 A1 | 2/2003 |
| EP | 1346831 A1 | 9/2003 |
| JP | 57145008 A | 9/1982 |
| WO | 0117897 A1 | 3/2001 |
| WO | WO 01/17897 A1 | 3/2001 |

OTHER PUBLICATIONS

Printout from website www.chemical-engineering-design.com/corrosion/probe.htm, CORROSION, Probe Mounting and Access Systems, 4 pages.
Printout from website www.armatek.com/HTMLPagesnoframes/rohrback.htm, Rohrback Cosasco Systems, 4 pages.
I. Al-Taie, Ph.D. Thesis, University of Manchester Institute of Science and Technology (UMIST), 1992, Manchester, England.
A. Chesnoy and D. Park, "S8 Threatens Natural Gas Operations, Environment," Oil and Gas Journal, Apr. 28, 1997.
B. Roberts, "The Effect of Sulfur Deposition on Gas Well Inflow Performance," SPE Annual Technical Conference and Exhibition, Denver, Colorado, SPE 36707, Oct. 1996.
S. C. Swift, F. S. Manning, and R. E. Thompson, "Sulfur-Bearing Capacity of Hydrogen Sulfide Gas," SPE Journal, Apr. 1976.
Arthur D. Little, Inc., Advanced Byproduct Recovery: Direct Catalytic Reduction of Sulfur Dioxide to Elemental Sulfur, Quarterly Report for U.S. Department of Energy, Office of Fossil Energy, [Online] Apr. 1997-Jun. 30, 1997, Morgantown, West Virginia.

* cited by examiner

DEVICE AND METHOD FOR MEASURING ELEMENTAL SULFUR IN GAS IN GAS LINES

RELATED APPLICATIONS

This nonprovisional patent application claims the benefit of provisional patent application U.S. Ser. No. 60/508,507, filed on Oct. 3, 2003, which is hereby incorporated by reference in its entirety.

BACKGROUND OF THE INVENTION

1. Technical Field

The present invention relates to the sampling of gases and, more particularly, to a device and method for measuring the level of elemental sulfur present in a gas in a gas line.

2. Description of the Related Art

Knowing of the presence of elemental sulfur in gas in a gas line is of high importance to engineers working with gas processing systems. Elemental sulfur vapor in a gas line can undergo condensation or deposition, either within the gas line or further downstream, and cause numerous problems, including unsafe, unreliable operations and increased maintenance costs. Condensed or deposed sulfur can cause corrosion acceleration and/or blockage by sulfur precipitates in process unit operations, which can interrupt the normal operation of the gas processing plant and, in some cases, require plant shutdown and diversion of the gas to another plant. These types of interruptions represent a safety hazard and often lead to environmental concerns. For example, if the blockage materials must be diverted to a burning pit, undesirable chemical fumes may be produced. In addition, the interruptions can be costly and often require manpower to locate and clear up blockage materials. Thus, it is desired to have the ability to measure the amount of elemental sulfur in gas in gas lines to avoid these and other problems.

Various devices and methods for measuring the amount of elemental sulfur present in gas in a gas line have been proposed; however, they have been ineffective and suffer from many disadvantages. For example, these devices and methods have not been able to provide accurate measurements, in part because elemental sulfur is usually present in extremely small quantities, i.e., parts per million or parts per billion. Also, available analytical techniques and instruments only measure the total sulfur present in the gas, and do not distinguish between free elemental sulfur and sulfur in other sulfur-containing chemicals, particularly in sour gas systems. Further, these previously proposed devices and methods are not particularly suitable for measuring elemental sulfur levels in gases in pressurized gas lines. In that regard, the use of sampling cylinders has been previously proposed. However, because elemental sulfur vapor condenses at temperatures below 52 degrees Celsius, when taking gas samples from pressurized gas pipelines for laboratory analysis, the sulfur condenses on the internal wall of the sampling cylinder, thus making sampling cylinders ineffective. Laboratory simulations have been performed and proposed. These simulations, however, have been performed in highly controlled environments and involve the evaporation of sulfur powder, and do not appear to be practical or accurate for real world applications involving, for example, pressurized gas streams.

Accordingly, prior to the development of the present invention, there has been no single device and method for measuring elemental sulfur in gas in gas lines which: provides an accurate measurement of elemental sulfur, can distinguish between free elemental sulfur and sulfur in other sulfur-containing chemicals, and is practical and effective when utilized in process plant applications, particularly in pressurized gas lines. Therefore, the art has sought a device and method for measuring elemental sulfur in gas in gas lines which: provides an accurate measurement of elemental sulfur, can distinguish between free elemental sulfur and sulfur in other sulfur-containing chemicals, and is practical and effective when utilized in process plant applications, particularly pressurized gas lines.

SUMMARY OF INVENTION

In accordance with the present invention, the foregoing advantages have been achieved through the present method for measuring the elemental sulfur present in gas in a gas line. This aspect of the present invention includes the steps of: collecting a sample of elemental sulfur-containing gas from the gas line, wherein the sample is collected on an outer surface of a probe by condensing some or all of the elemental sulfur-containing gas in the gas line on a surface of the probe while the gas line is operational, the probe being removably placed into a gas flow stream from the gas line; separating the elemental sulfur from other species in the sample into an amount of elemental sulfur; and analyzing the amount of elemental sulfur collected. A preferred embodiment of the present invention includes cooling the probe to promote condensation of gas vapors on the outer surface of the probe. A preferred embodiment of the present invention includes using an internal coolant, which is a coolant internal to the probe, to cool the probe. A preferred embodiment of the present invention is that the internal coolant is cooling water. A preferred embodiment of the present invention is that the step of separating the elemental sulfur from other species in the sample further includes: washing the probe with solvent to remove essentially all species on the outer surface of the probe except elemental sulfur; submerging the probe in carbon disulfide; dissolving the elemental sulfur on the probe in the carbon disulfide; and evaporating the carbon disulfide.

In accordance with another aspect of the present invention, the foregoing advantages have also been achieved through the present method for measuring the level of elemental sulfur in gas flowing in a gas line. This aspect of the invention may include the steps of: inserting a probe into a gas flow stream from the gas line; collecting a sample of condensable components from the gas on the outer surface of the probe; removing the probe from the gas flow stream from the gas line; separating the elemental sulfur in the sample from other species present in the sample to form an amount of elemental sulfur; and analyzing the amount of elemental sulfur collected. A preferred embodiment of the present invention includes cooling the probe to promote condensation of gas vapors on the outer surface of the probe. A preferred embodiment of the present invention is that an internal coolant is used to cool the probe. A preferred embodiment of the present invention is that the internal coolant is cooling water.

In accordance with another aspect of the present invention, the foregoing advantages have also been achieved through the present device for collecting condensed sulfur from a gas line. The present invention may include: an access fitting detachably connectable with the gas line, the access fitting having a first end and a second end; a probe detachably connectable to at least one end of the access fitting and adapted for insertion into a gas flow stream from the gas line to recover condensed components on the probe's outer surface; and a piping partially disposed within the probe for providing a cooling medium to the probe. A preferred embodiment of the present invention is that an outer housing detachably connectable with at least one end of the access fitting. A preferred embodiment of the present invention is that the piping is disposed within the outer housing, the access fitting, and the probe. A preferred embodiment of the present invention is that the outer housing has a piping inlet and a piping outlet. A preferred embodiment of the present invention is that the access fitting is an industry standard size.

In accordance with another aspect of the present invention, the foregoing advantages have also been achieved through the present device for collecting condensed sulfur from a gas line, the gas line having one or more sampling points disposed thereupon. The present invention may include a probe casing; a probe detachably connectable to the probe casing and adapted for insertion into a gas flow stream from the gas line to recover condensed components on the probe's outer surface; a first tubing segment disposed between the probe casing and a sampling point on the gas line for delivering gas from the gas line to the probe casing; and a second tubing segment disposed between the probe casing and a sampling point on the gas line for delivering gas devoid of recovered condensed components from the probe casing to the gas line. A preferred embodiment of the invention includes a piping partially disposed within the probe for providing a cooling medium to the probe.

The device and method of the present invention for measuring the level of elemental sulfur present in a gas in a gas line, when compared with previously proposed devices and methods, has the advantages of: providing an accurate measurement of elemental sulfur, being able to distinguish between free elemental sulfur and sulfur in other sulfur-containing chemicals, and being practical and effective for use in process plant applications, particularly pressurized gas lines.

While the invention will be described in connection with the preferred embodiment, it will be understood that it is not intended to limit the invention to that embodiment. On the contrary, it is intended to cover all alternatives, modifications, and equivalents as maybe included within the spirit and scope of the invention as defined by the appended claims.

DETAILED DESCRIPTION OF THE PREFERRED EMBODIMENT OF THE PRESENT INVENTION

Figure 1:
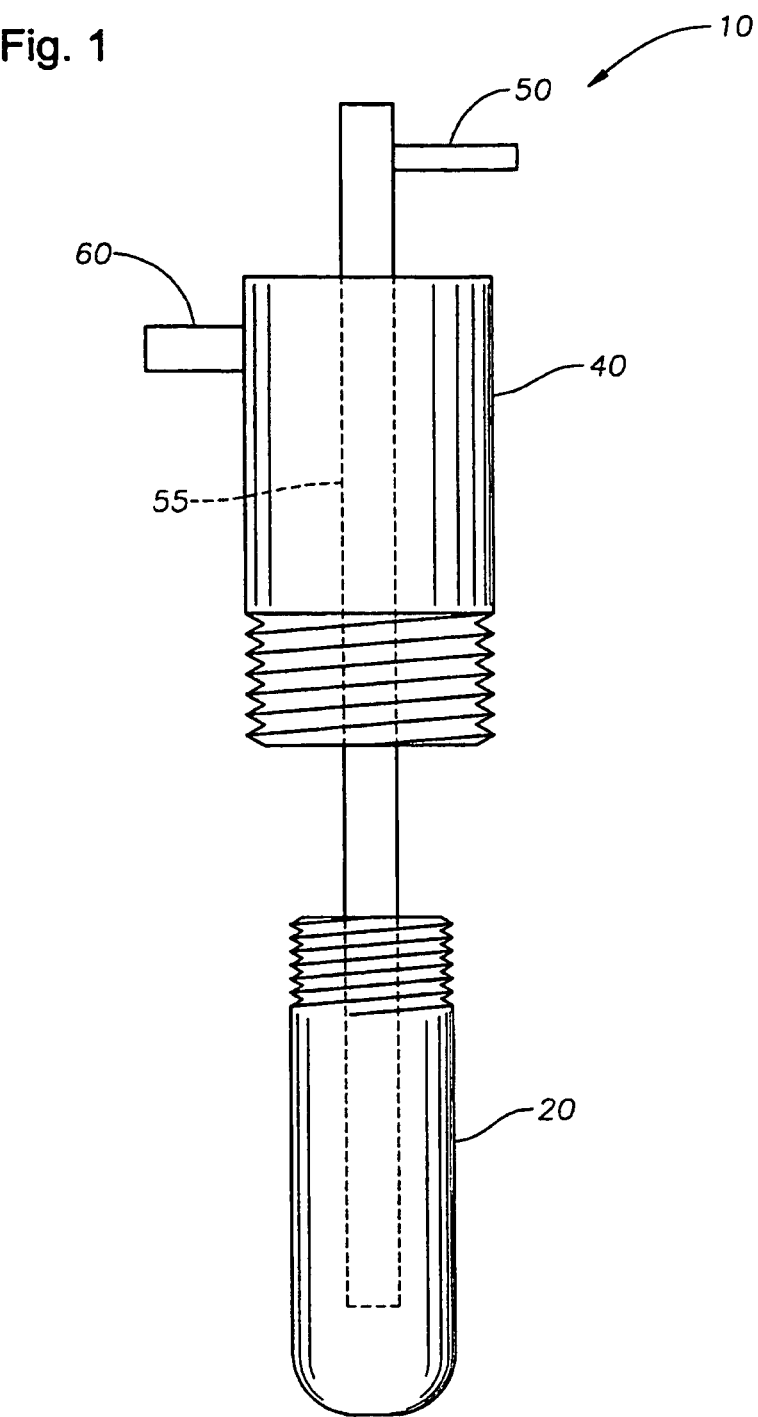
FIG. 1 is a partial sectional view of a device for measuring elemental sulfur in a gas in a gas line in accordance with an embodiment of the present invention.
Figure 2:
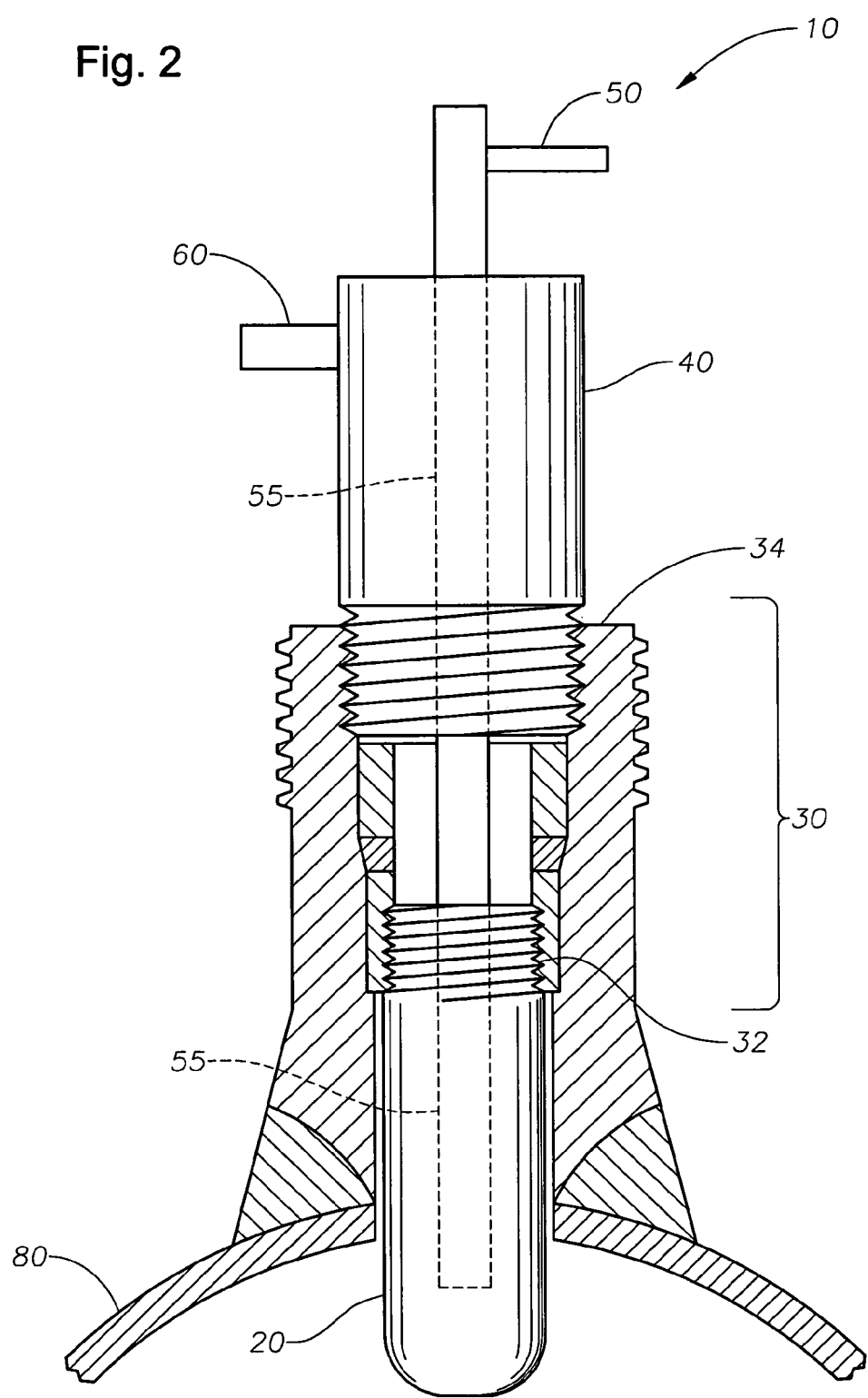
FIG. 2 is a partial sectional view of a device for measuring elemental sulfur in a gas attached to an access fitting on a gas line in accordance with an embodiment of the present invention.

In FIG. 1, a device 10 for measuring the elemental sulfur present in gas in a gas line in accordance with the present invention is shown. The device 10 includes a specially designed probe 20 that is preferably about 1.3" in diameter and preferably either about 3", 5" or 8" in length. The probe 20 engages with the bottom of a standard 2" access fitting 30 (FIG. 2), such as, for example, a COSASCO® fitting, that is attached to a gas line. Preferably, the probe 20 fits in the bottom of the access fitting 30 (FIG. 2), and the outer surface of the probe 20 is exposed within the gas line. In certain embodiments, the gas line will be pressurized. The device 10 also includes an upper section 40 that engages with the top of the access fitting 30 (FIG. 2). Preferably, the upper section 40 fits into the top of the access fitting 30 (FIG. 2). An internal coolant, for example cooling water, enters the device 10 at or near the top of the upper section 40 through coolant piping 55. In the preferred embodiment shown in FIG. 1, coolant piping 55 passes through both the upper section 40 and the access fitting 30 (FIG. 2) to supply cooling water to the probe 20. Cooling water enters coolant piping 55 through inlet pipe 50, which is preferably about ¼" in diameter. The cooling water is released within the interior of probe 20 and cools the outer surface of probe 20. In the embodiment shown, an ice chest or other cooling mechanism can be used to reduce the temperature of the cooling water in coolant piping 55. However, other mechanisms for cooling and providing temperature control for the components of device 10 could be utilized. The cooling water exiting the probe 20 leaves the device 10 through a coolant outlet pipe 60 in the upper section 40 that is preferably about ¼" in diameter.

FIG. 2 illustrates a preferred embodiment of the device as would typically be seen in a gas processing facility. A standard 2" access fitting 30 is attached to a gas line 80. The access fitting shown in FIG. 2 is a COSASCO®-type fitting. The probe 20 is attached to the bottom portion 32 of the access fitting 30 and partially disposed within the interior of gas line 80 so as to contact a gas flow stream within the gas line 80. The upper section 40 of the device 10 is attached to the upper portion 34 of the access fitting 30.

The procedure for measuring the amount of elemental sulfur in the gas line 80 involves attaching the device 10 to the gas line 80 via the standard access fitting 30, with the probe 20 partially disposed inside the gas line 80. A condensed gas sample from the gas line 80 is collected on the outer surface of the probe 20. The device 10 utilizes a "cold finger" concept, wherein coolant piping 55 is used to cool the probe 20 to a temperature that allows vapor in the gas line 80 to condense and collect on the outer surface of the probe 20. Once the probe 20 is disposed within the gas line 80, it should preferably remain in this location for at least twenty-four (24) hours to allow as much exposure to the gas within the gas line 80 as possible. After at least twenty-four (24) hours of exposure, the probe 20 should be removed from the gas line 80. The probe 20 should be visually examined for the presence of any liquid condensates. Any such condensates should be dissolved in an organic solvent that does not dissolve sulfur, preferably xylene (dimethylbenzene), to remove all condensed species from the outside of the probe 20 except elemental sulfur. In a preferred embodiment, the removed condensed species are hydrocarbons of $C_{6+}$. Once the liquid condensates are dissolved, the probe 20 should be submerged in or sprayed with carbon disulfide ($CS_2$) in a preweighed container to dissolve the elemental sulfur. Preferably, around 250-500 ml of carbon disulfide ($CS_2$) should be used, depending on the size of the probe 20. This procedure should be carried out inside a fume hood with good ventilation. Once the elemental sulfur has dissolved, the probe 20 should be removed from the container, and the $CS_2$ should be allowed to evaporate naturally without heating, leaving only elemental sulfur in the container. Once all the $CS_2$ has evaporated, the container and its contents should be weighed. The difference between the weight of the container and its contents and the original pre-weighed weight of the container alone represents the amount of sulfur collected from the gas line 80 during the twenty-four (24) hour exposure period. This result can be used to determine the level of sulfur per volume of gas in the gas line 80 by calculating the surface area of the probe 20 and estimating the volume of gas passed on the calculated area during the twenty-four (24) hours of exposure.

Figure 3:
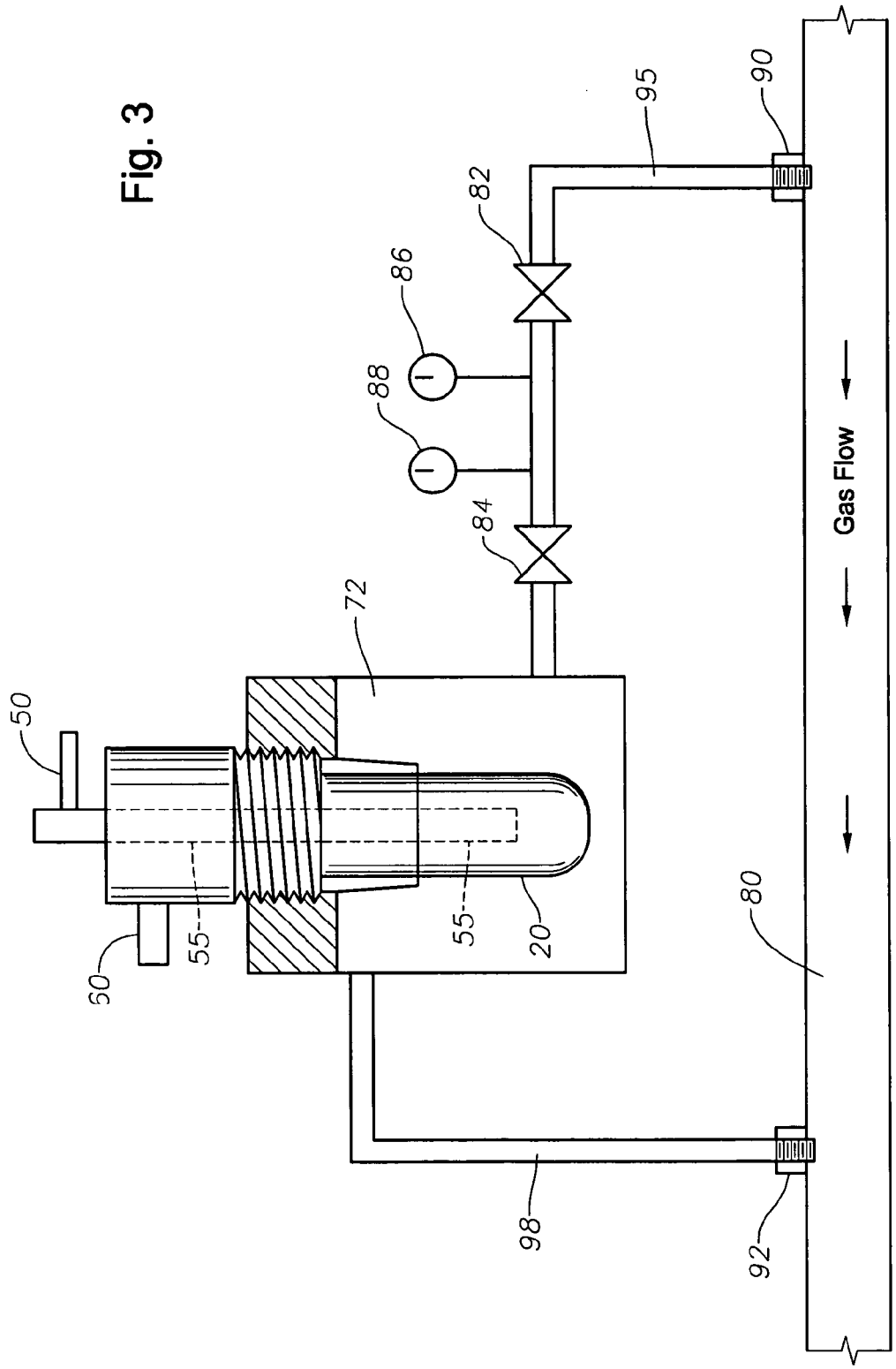
FIG. 3 is a partial sectional view of a device for measuring elemental sulfur in a gas attached to sampling points or vent points on a gas line in accordance with an embodiment of the present invention.

FIG. 3 illustrates an embodiment of the present invention in which sampling points or vent points 90, 92 are utilized to obtain a sample of elemental sulfur from a gas in a gas line 80. The sampling points or vent points 90, 92 are used when the gas line 80 does not have access fittings such as COSASCO®-type fittings, or the access fittings are installed in inconvenient or inappropriate positions. The sampling points or vent points 90, 92 allow a gas flow stream from the gas line 80 to exit the gas line 80, flow through external tubing 95, contact probe 20 and flow through additional external tubing 98 and reenter gas line 80. According to this embodiment, gas from the pressurized gas line 80 enters a first sampling point or vent point 90. Sampling point or vent point 90 is preferably detachably connected to tubing 95. The gas passes from sample point 90 into tubing 95. While in the tubing 95, the gas pressure is reduced using pressure regulator 82, preferably to approximately 30 psi. Gas pressure in the tubing 95 can be monitored using, for example, a pressure gauge 86. At approximately 30 psi, the elemental sulfur in the gas is at or near its condensation point. The reduced pressure gas is delivered to a probe casing 72 with a probe 20 positioned therein. Preferably, the gas enters near the bottom of probe casing 72, and the elemental sulfur from the gas, which is at or near its condensation point, condenses on the outer surface of the probe 20. Preferably, the probe 20 can be removed from the probe casing 72 so that the elemental sulfur sample that has collected on the outer surface of the probe 20 can be recovered. Preferably, the pressure reduction occurring at pressure regulator 82 will alone be sufficient to allow the elemental sulfur to condense on the outer surface of the probe 20. If, however, additional cooling is needed to promote condensation, the outer surface of the probe 20 can be cooled with, for example, cooling water, using the "cold finger" concept as described previously herein. Once the elemental sulfur has condensed on the probe 20, the remaining uncondensed gas exits the probe casing 72, preferably near the top of the casing 72, and is transported through tubing 98 to a second sampling point or vent point 92 to be deposited back into the gas line 80. In certain embodiments, first sampling point 90 and second sampling point 92 can be the same sampling point.

Preferably, the flow rate of gas within tubing 95 is regulated using a flow meter 84 and monitored by, for example, a flow gauge 88. Preferably, the gas flow rate will be approximately 150 ml/min. Using this approximate flow rate, a probe 20 installed using sampling lines or vent points 90, 92 according to an embodiment of the present invention can detect elemental sulfur in a gas in parts per million within twenty four (24) hours of exposure.

It is to be understood that the invention is not limited to the exact details of construction, operation, exact materials or embodiments shown and described, as obvious modifications and equivalents will be apparent to one skilled in the art. Accordingly, the invention is therefore to be limited only by the scope of the appended claims.

The invention claimed is:

1. A system for collecting condensed sulfur from a gas line comprising:
   a device comprising:
      an access fitting detachably connectable with the gas line, the access fitting having a first end and a second end,
      a probe detachably connectable to at least one end of the access fitting and adapted for insertion into a gas flow stream from the gas line and configured to collect condensed components on the probe's outer surface without allowing the gas flow stream to flow through the probe, wherein the condensed components comprise the condensed sulfur, and
      a piping partially disposed within the probe for providing a cooling medium to the probe;
   a first tubing segment disposed between the device and a first sampling point on the gas line configured to deliver gas from the gas line to the device; and
   a second tubing segment disposed between the device and a second sampling point on the gas line configured to deliver gas devoid of recovered condensed components from the device to the gas line,
   wherein the first tubing segment comprises a pressure reduction valve configured to reduce a pressure of the gas such that the sulfur in the gas condenses on the probe's outer surface.

2. The system of claim 1, wherein the access fitting is an industry standard size.

3. The system of claim 1, wherein the piping is not in fluid communication with the gas flow stream.

4. A system for collecting condensed sulfur from a gas line, the gas line having a first sampling point and a second sampling point disposed thereupon, the system comprising:
   a device comprising:
      a probe casing, and
      a probe detachably connectable to at least one end of the probe casing and adapted for insertion into a gas flow stream from the gas line and configured to collect condensed components on the probe's outer surface without allowing the gas flow stream to flow through the probe, wherein the condensed components comprise the condensed sulfur;
   a first tubing segment disposed between the probe casing and the first sampling point on the gas line configured to deliver gas from the gas line to the probe casing; and
   a second tubing segment disposed between the probe casing and the second sampling point on the gas line configured to deliver gas devoid of recovered condensed components from the probe casing to the gas line,
   wherein the first tubing segment comprises a pressure reduction valve configured to reduce a pressure of the gas such that the sulfur in the gas condenses on the probe's outer surface, and wherein the device further comprises a piping partially disposed within the probe for providing a cooling medium to the probe.

5. The system of claim 4, wherein the piping is not in fluid communication with the gas flow stream.

6. A system for collecting condensed sulfur from a gas line comprising:
   a device comprising:
      a probe configured to be detachably connectable to a bottom portion of an access fitting and to be inserted into a gas flow stream from the gas line, the probe being configured to collect condensed components on the probe's outer surface without allowing the gas flow stream to flow through the probe, wherein the condensed components comprise the condensed sulfur,
      an upper section having an interior annular portion, the upper section being operable to engage a top portion of the access fitting,
      a piping internally disposed within the interior annular portion of the upper section and the probe, such that the piping is operable to deliver a cooling medium to the interior portion of the probe, wherein the piping is not in fluid communication with the gas in the gas line, a cooling medium inlet in fluid communication with the piping, and
a cooling medium outlet in fluid communication with the interior annular portion of the upper section;
a first tubing segment disposed between the device and a first sampling point on the gas line configured to deliver gas from the gas line to the device; and
a second tubing segment disposed between the device and a second sampling point on the gas line configured to deliver gas devoid of recovered condensed components from the device to the gas line,
wherein the first tubing segment comprises a pressure reduction valve configured to reduce a pressure of the gas such that the sulfur in the gas condenses on the probe's outer surface.

7. A system for collecting condensed sulfur from a gas line comprising:
a device comprising:
an access fitting detachably connectable with the gas line, the access fitting having a first end and a second end,
a probe detachably connectable to at least one end of the access fitting and adapted for insertion into a gas flow stream from the gas line and configured to collect condensed components solely on the probe's outer surface, wherein the condensed components comprise the condensed sulfur, and
a piping partially disposed within the probe for providing a cooling medium to the probe;
a first tubing segment disposed between the device and a first sampling point on the gas line configured to deliver gas from the gas line to the device; and
a second tubing segment disposed between the device and a second sampling point on the gas line configured to deliver gas devoid of recovered condensed components from the device to the gas line,
wherein the first tubing segment comprises a pressure reduction valve configured to reduce a pressure of the gas such that the sulfur in the gas condenses on the probe's outer surface.

* * * * *